United States Patent [19]

Grandi

[11] Patent Number: 4,987,069

[45] Date of Patent: Jan. 22, 1991

[54] **NUCLEOTIDE SEQUENCE CAPABLE OF INDUCING HIGH LEVELS OF TRANSLATION OF A HETEROLOGOUS GENE IN *BACILLUS SUBTILIS* AND *ESCHERICHIA COLI***

[75] Inventor: Guido Grandi, Segrate, Italy

[73] Assignee: Eniricerche S.p.A., Milan, Italy

[21] Appl. No.: 40,612

[22] Filed: Apr. 21, 1987

[30] Foreign Application Priority Data

May 7, 1986 [IT] Italy .............................. 20344 A/66

[51] Int. Cl.$^5$ ...................... C12P 21/00; C14N 15/00; C07H 15/12
[52] U.S. Cl. .................. 435/69.1; 435/172.3; 435/252.31; 435/320.1; 435/231; 536/27; 935/29; 935/44; 935/45; 935/46; 935/73; 935/74
[58] Field of Search .................. 435/320, 353, 68, 91; 935/29, 44, 45, 46, 73, 74; 536/27

[56] References Cited

U.S. PATENT DOCUMENTS 4,529,695 7/1985 Weisblum .......................... 935/29 X
4,626,510 12/1986 Grandi ............................... 935/27 X

OTHER PUBLICATIONS

Kiss, A. et al, *Nuc. Acids Res.*, vol. 13, pp. 6403-6421, 1985.
Stahl, M. et al, *J. Bacteriology*, vol. 158, pp. 411-418, 1984.
Breunig, K. et al, *Gene* 20, pp. 1-10, 1982.
Roberts, T. et al, *Proc. Natl. Acad. Sci.*, vol. 76, pp. 760-764, 1979.
Grandi, G. et al, *Plasmid*, vol. 16, pp. 1-14, Jul. 1986.

*Primary Examiner*—Richard A. Schwartz
*Assistant Examiner*—Larry Millstein
*Attorney, Agent, or Firm*—Hedman, Gibson, Costigan & Hoare

[57] ABSTRACT

Nucleotide sequences capable of inducing high levels of translation of a heterologous gene in *Bacillus subtilis* and *Escherichia coli* and a method of preparing heterologous proteins comprising cultivation in a suitable culture medium of cells of *Bacillus subtilis* and *Escherichia coli* transformed by hybrid plasmids in which the nucleotide sequence is situated between the ribosome recognition site and the starting triplet (ATG) of the coding structural gene for the desired proteins.

4 Claims, 4 Drawing Sheets

NUCLEOTIDE SEQUENCE CAPABLE OF INDUCING HIGH LEVELS OF TRANSLATION OF A HETEROLOGOUS GENE IN BACILLUS SUBTILIS AND ESCHERICHIA COLI

The invention relates to a nucleotide sequence capable of inducing high levels of translation of a heterologous gene in *Bacillus subtilis* and *Escherichia coli* and a method of preparing heterologous proteins comprising cultivation, in a suitable culture medium, of cells of *Bacillus subtilis* and *Escherichia coli* transformed by hybrid plasmids in which the nucleotide sequence is situated between the ribosome recognition site and the starting triplet (ATG) of the coding structural gene for the desired protein.

In procaryotes, the expression of a gene (i.e. the process of transcription and translation whereby genetic information is used for synthesizing proteins) is controlled by regulating regions. These regions, which are represented at DNA level by certain sequences of nucleotide bases, comprise: the promotor, the terminator, the ribosome recognition site (RBS) and the triplets for starting (ATG) and stopping the translation.

The term "transcription" means the transfer of genetic information from DNA to messenger RNA (mRNA).

This process, which is brought about by a specific enzyme (DNA-dependent RNA-polymerase), initiates in the promotor a region which is located upstream of the coding structural gene for a given protein and which contains a recognition site and an attachment site for the RNA-polymerase.

The transcription terminates in a region situated at the end of the structural gene, called terminator. The terminator ensures that the RNA-polymerase is detached from the DNA.

Once the genetic information has been transcribed in the m-RNA, it is used for synthesizing proteins or, more generally, is translated into protein.

The term "translation" denotes transfer of genetic information from mRNA to the protein in accordance with the rules of the genetic code.

The translation begins via the bond between the ribosomes and the ribosome recognition site of mRNA, whose nucleotide sequence on the DNA is situated behind the promotor.

The triplets for starting (ATG) and stopping the translation show the associated ribosomes and enzymes where the genetic message starts and stops respectively.

The primary sequence of a protein is determined by codons, which are present between the ATG and the stop triplet.

The structure of a gene is rigorously preserved as described hereinbefore and shown in FIG. 1, and this guarantees the complex sequence of events resulting in the synthesis of the protein.

As is known, the greater the affinity between RNA-polymerase and the promotor and the ribosome and RBS, the more efficient is the transcription and translation of a given gene. The technical literature gives nucleotide sequences, in the case both of the promotor and of the RBS, which can guarantee good affinity between the aforementioned structures. In the case, for example, of RBS, the optimum sequence given is AAAGGAGG, complementary with the third terminal of ribosomal 16S RNA.

Particular importance, in the expression of a gene, also attaches to the composition and number of bases in the spacing sequence interposed between the RBS and the starting ATG of the gene. Recent developments in genetic engineering have made it possible to prepare a protein by the cloning technique, in which the coding gene for the protein is joined to a suitable cloning vector, the resulting hybrid vector is inserted into a host microorganism, and finally the transformed microorganism is cultivated so as to produce the desired protein. More particularly, the technique can be used to improve the preparation of a protein by cloning the coding gene for the protein, under the control of optimum regulating regions.

Known sequences can be used for the promotor and RBS, but it is still difficult to foresee the spacing sequence capable of optimizing the expression of a given gene.

A nucleotide sequence has now been found for obtaining high translation levels of heterologous genes in *Bacillus subtilis* and in *Escherichia coli*.

Accordingly, one aim of the invention is a nucleotide sequence capable of inducing high translation levels of a heterologous gene in *Bacillus subtilis* and *Escherichia coli*.

Another aim of the invention is a method of preparing heterologous proteins comprising cultivation in a suitable culture medium of cells of *Bacillus subtilis* and *Escherichia coli* transformed by hybrid plasmids in which the nucleotide sequence is situated between the ribosome recognition site and the starting triplet ATG of the structural gene which codes the protein.

Other aims of the invention will be clear from the following description and examples.

More particularly, according to the invention the nucleotide sequence is:

$$\begin{array}{l} \text{G T T A A T T C T} \\ \text{C A A T T A A G A} \end{array} \quad (I)$$

where
- A = adenine
- C = cytosine
- G = guanine and
- T = thymidine.

This sequence, which occurs between the ribosome recognition site and the starting ATG of a heterologous gene, ensures a high rate of translation of the gene. Beta-lactamase, methylase and the human growth hormone are examples of heterologous genes which can be cloned.

According to the invention, the nucleotide sequence (I) was inserted between the RBS and the ATG of the coding gene for beta-lactamase and the resulting hybrid plasmid was used to transform cells of *Bacillus subtilis* and *Escherichia coli*. Surprisingly, it has been found that the production of beta-lactamase shows a notable improvement in both microorganisms.

More particularly, the nucleotide sequence (I) was inserted into plasmid pSM143 ATCC 53038, whose restriction map is shown in FIG. 2, where the coding gene for beta-lactamase is under the control of regulating, promotor and RBS sequences recognized by *B. subtilis* and *E. coli* and where the spacing sequence is AATTCT.

Plasmid pSM143 was digested with the restriction enzyme EcoRI, which cuts the DNA immediately after RBS and leaves ends with a single helix.

The digestion mixture was then mixed with the polymerase enzyme and kept at a temperature between 10° and 20° C. until the polymerisation reaction was complete.

This operation resulted in completing the single helices and lengthening the chain.

After the polymerase had been inactivated, the reaction mixture was again digested with the restriction enzyme XbaI, in a buffer solution at a temperature between 30° and 40° C.

At the end of the reaction, the mixture was placed on 6% acrylamide gel and treated at 110 V for 3 hours. The 6600 base-pair fragment containing the beta-lactamase gene was then electro-eluted and bonded to the approximately 750 base-pair fragment XbaI-HpaI containing the promotor and RBS of the plasmid of Bacillus subtilis pE194 (BGSG 1E7).

The last-mentioned fragment was obtained by digestion of plasmid pSM26, whose restriction map is shown in FIG. 3 and whose construction has recently been described by Grandi et al in Plasmid 1986 (in course of publication).

The ligase reaction between the two fragments was brought about in the presence of T4 DNA ligase at a temperature of 10° to 20 ° C.

At the end of the reaction, the ligase mixture was used to transform suitable cells of E. coli and the transforming substances were selected for ampicillin resistance (Amp®). The hybrid plasmid pSM164, which was isolated from one of the Amp® clones, has a nucleotide sequence, determined by the method of Maxam and Gilbert (Methods in Enzymology, Vol. 65, 1980), which shows the presence of the spacing sequence (I) between the RBS region and the ATG of the beta-lactamase gene. According to the invention, the hybrid plasmid pSM164 was used to transform cells of Bacillus subtilis and Escherichia coli.

More particularly, use was made of cells of B. subtilis SMS118 (leu, pwrD1, npr−, spr−) and of E. coli HB101 described by T. Maniatis in Molecular Cloning: A Laboratory Manual, 504 Cold Spring Harbor 1982. The cells were transformed as described respectively by Contente and Dubnau (Mol.Gen.Genet., 167, 251–258 (1978)) and by Mandel and Higa (J.Mol. Biol.53, 159–162, 1970).

The transformed cells were cultivated in VY liquid medium (DIFCO) mixed respectively with 5 μg/ml and 50 μg/ml of kanamycin at a temperature of 30° to 40° C.

The production of beta-lactamase was measured by analysis of the beta-lactamase activity by the method described by O'Callaghan et al (Antimicrob. Ag. Chemother. I (1972) 283–288). According to the invention, the spacing sequence (I) was compared with other spacing sequences, more particularly pSM143 and pSM162 (AATAATTCT), a plasmid constructed from pSM143 and having the restriction map shown in FIG. 3 and the construction described in example 2. Cells of B. subtilis SMS118 and E. coli HB101 transformed by these plasmids were cultivated under the conditions used for microorganisms transformed with pSM164. The results, expressed as beta-lactamase activity, show five times the activity obtained for the other transformed strains, in the case both of B. subtilis SMS118 (pSM164) and E. coli HB101 (pSM164).

Since the promotor sequence is the same in plasmids pSM143, pSM162 and pSM164, the difference in activity can be attributed only to a different efficiency of translation.

Furthermore, since the RBS region is identical in the three plasmids and the difference in spacing does not appreciably change the ΔG of formation of the bond between the ribosomal 16SRNA and the mRNA calculated by Tinoco's rules (Nature New.Biol. 246, 40–41 (1973), it appears that the affinity of the ribosomes for the three mRNA's is identical. Furthermore, measurements based on Tinoco's calculations have not shown appreciable variations in the ΔG of formation of secondary structures of the mRNA of the beta-lactamase in the three plasmids.

Accordingly, it appears that the spacing sequence (I) is optimum for the translation process for either B. subtilis or E. coli.

The strain B. subtilis SMS118(pSM164) was deposited at the American Type Culture Centre on April, 18, 1986, No. ATCC-67098.

The following experimental examples non-limitatively illustrate the invention.

EXAMPLE 1

Construction of pSM164

10 μg of pSM143 were digested with 10 units (U) of EcoRI (Boehringer) restriction enzyme in 50 μl of reaction volume at 37° C. for 1 hour, under the conditions described by the producing firm.

After inactivation of the enzyme at 65° C. for 10 minutes, 5 μl of the reaction mixture were added to 45 μl of a solution containing 50 mM Tris-HCl (pH 7.5), 5 mM MgCl₂, 100 μm dATP, 100 μm dTTP and 4 U of polymerase (Klenow fragment, Boehringer).

The polymerisation reaction was carried out at 14° C. for 2 hours. At the end of the reaction, the enzyme was inactivated at 65° C. for 10 minutes.

50 μl of reaction mixture were mixed with NaCl to a final concentration of 50 mM and with 1 U of XbaI (Boehringer) enzyme, and the resulting mixture was incubated at 37° C. for 1 hour.

After inactivation of the enzyme at 65° C. for 10 minutes, the plasmid DNA was placed on 6% agarose gel and treated at 110 V for 3 hours. The band containing the 6600 bp fragment of pSM143 carrying the beta-lactamase gene was eluted as described by Maniatis et al (Molecular Cloning: A Laboratory Manual. Cold Spring Harbor p. 170 (1982)).

The plasmid DNA was then precipitated by adding 0.3 M sodium acetate and 2.5 volumes of 95% ethanol to the eluate.

The resulting suspension was centrifuged in a modified Epperdorf centrifuge for 10 minutes at 11,000 revolutions per minute (rpm). The DNA was separated and re-suspended in a buffer solution at a final concentration of 0.5 μg/ml.

10 μg of pSM 26 were digested at 37° C. for 1 hour in 50 μl of solution containing 50 mM Tris-Hcl (pH 7.5), 5mM MgCl₂, 50 mM NaCl, 10 U of XbaI and 10 U of HpaI.

After inactivation of the enzymes, the DNA was separated on acrylamide gel and the approximately 750 bp fragment containing the promotor and RBS of pE194 was electro-eluted as described by Maxam and Gilbert (Methods in Enzymology, Vol. 80 (1980)). The DNA was precipitated from the eluate, separated and re-suspended in buffer solution at a concentration of 0.5 µg/ml.

0.1 µg of the 6600 bp DNA fragment were bonded to 30 ng of the 750 bp XbaI-HpaI fragment in a solution containing 66 mM Tris-HCL (pH 7.5), 10 mM $MgCl_2$, 10 mM dithiothreitol, 1 mM ATP and 1 U of T4 DNA ligase (Boehringer) at 14° C. for 18 hours. After inactivation of the enzyme, 5 µl of the ligase mixture were used to transform cells of E. coli HB101 and the transforming substances were selected for resistance to ampicillin on LB Agar plates (DIFCO) mixed with 50 µg/ml ampicillin.

Figure 1:
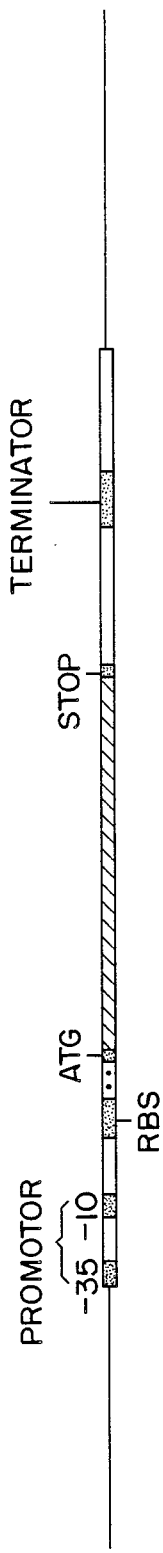
FIG. 1: Structure of a procaryote gene.
Figure 2:
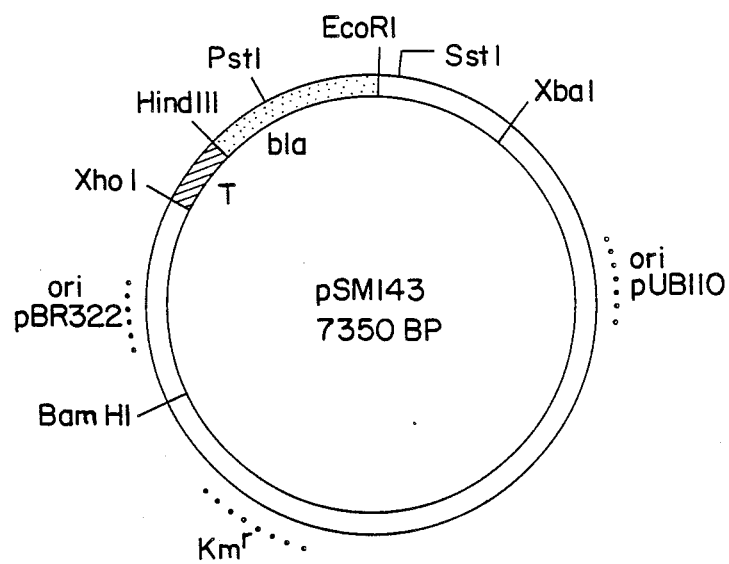
FIG. 2: Restriction map of plasmid pSM143.
Figure 3:
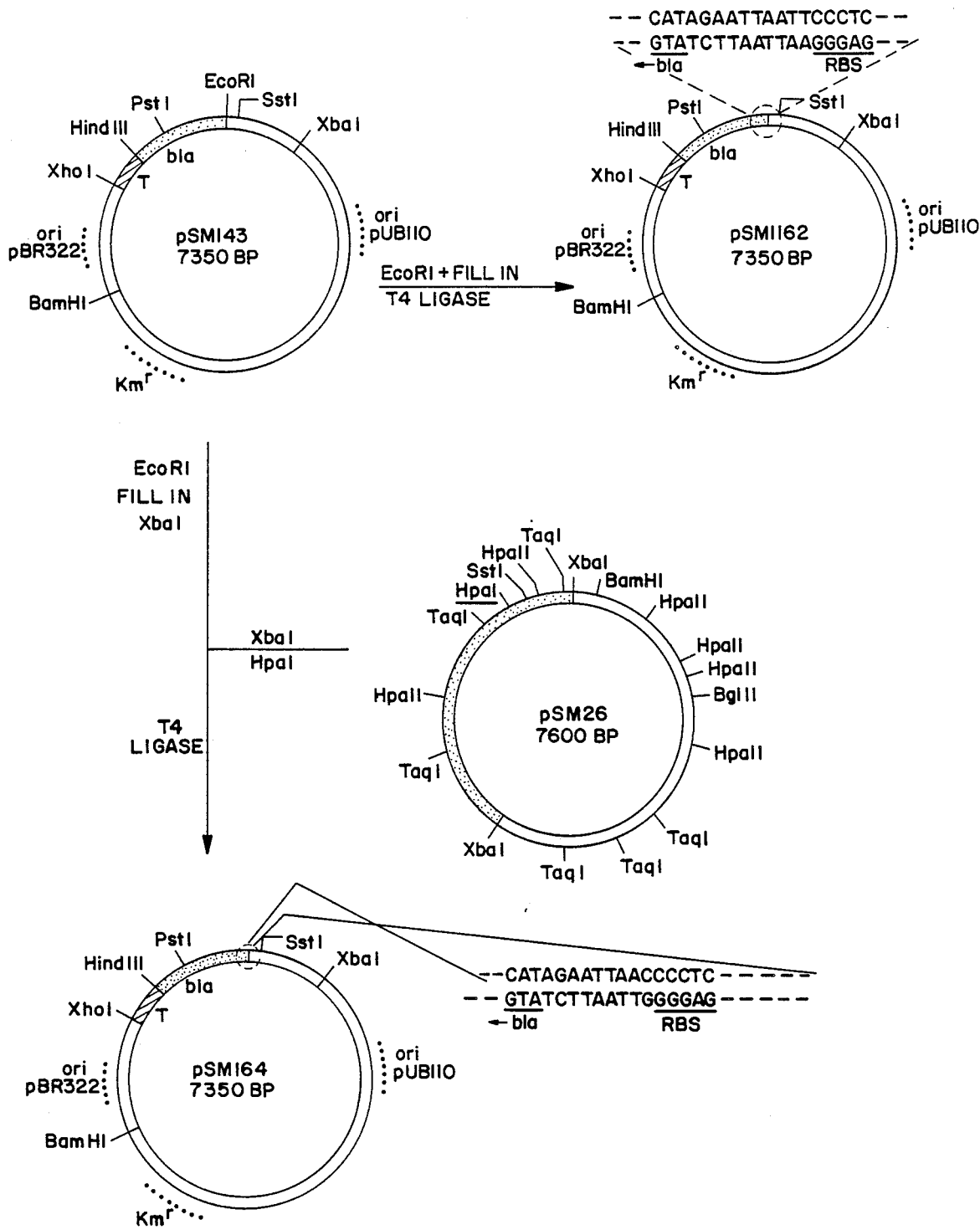
FIG. 3: Diagram of the construction of pSM162 and pSM164.
Figure 4:
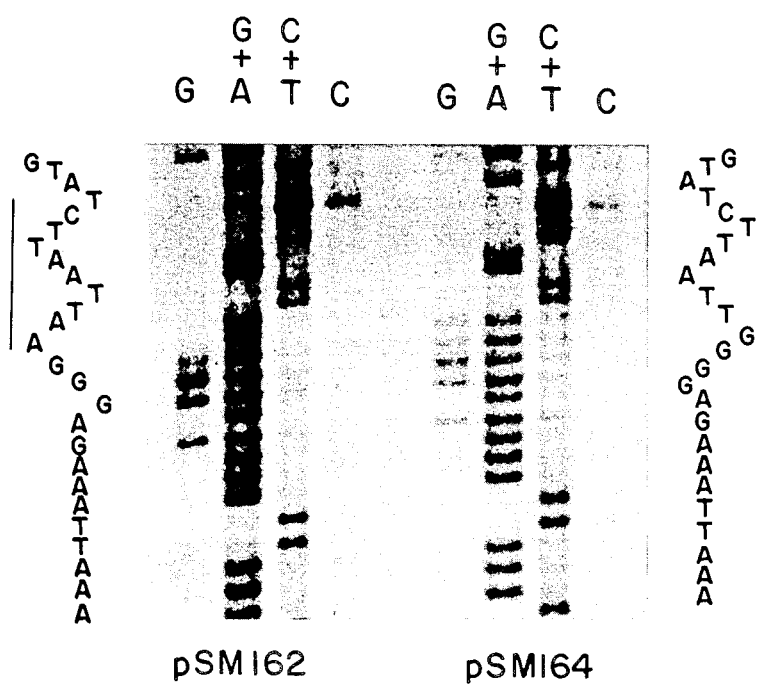
FIG. 4: Analysis of the sequence of spacing regions of pSM162 and pSM164.

Plasmid pSM164, the restriction map of which is shown in FIG. 3, was isolated from an ampicillin-resistant colony. Analysis of the nucleotide sequence of pSM164 showed the presence of the desired spacing sequence (FIG. 4) between the RBS region and the starting ATG of the beta-lactamase gene.

EXAMPLE 2

Construction of pSM162

1 µg of pSM143 was digested as described in Example 1 and, after inactivation of the enzyme, were added to 48 µl of a solution containing 50 mM Tris-HCl (pH 7.5), 5 mM $MgCl_2$, 100 µm of ATP, 100 µm of dTTP and 2 U of polymerase. The polymerisation reaction was carried out at 14° C. for 1 hour, after which the enzyme was inactivated by mixing the reaction mixture with an equal volume of phenol saturated with TE (10 mM Tris-HCL (pH 7.5) and 1 mM EDTA). The phenol dissolved in the aqueous phase was subsequently extracted with ether and the DNA was precipitated at −80° C. by adding 5 µl of a 3M solution of sodium acetate and 250 microliters of 95% ethanol.

The precipitate was separated by centrifuging, dried in vacuo and resuspended in 50 µl of a solution of 66 mM Tris-HCl (pH 7.5), 6 mM $MgCl_2$, 10 mM dithiothreitol, 1 mM dATP and 1 U of T4 DNA ligase.

The mixture was incubated at 14° C. for 18 hours, after which 10 µl were used to transform suitable cells of E. coli HB101 selected for ampicillin resistance as described in Example 1.

Plasmid pSM162, the restriction map of which is shown in FIG. 3, was isolated from one of the resulting positive clones.

The nucleotide sequence of the region nearest to the beginning of the beta-lactamase gene shows the following spacing, as expected:

```
A A T T A A T T C T
T T A A T T A A G A
```

EXAMPLE 3

Comparison between the beta-lactamase activity of strains of E. coli and B. subtilis transformed by plasmids pSM143, pSM164 and pSM162

Transformed cells of B. subtilis pSM118 and E. coli HB101 were cultivated in lactose broth (DIFCO) in the presence respectively of 15 µg/ml and 5 µg/ml kanamycin at 37° C. until the optical density measured at 660 nm was about 2.5-3.1.

The production of beta-lactamase was measured in the case of E. coli in the periplasmatic preparations obtained as described by A. Nicolaids (J. Bacteriol. 135, 178 (1978)) whereas in the case of B. subtilis, production was determined in the cellular sonicated substances.

More particularly, the sonicates were prepared by suspending the B. subtilis cells, separated from the broth culture by centrifuging, in 5 ml of solution containing 30 mM Tris-HCl (pH 7.2) and 50 mM NaCl. The cellular suspension was re-centrifuged at 5000 rpm for 10 minutes and the cells were resuspended in phosphate buffer (pH 7.0) and lysed in a Soniprep 150 model MSE sonicator operating at the maximum velocity.

The beta-lactamase activity was measured as described by O'Callaghan et al. Antimicrob.Ag.-Chemother. I,283-288 (1972) and expressed as units per ml, i.e. as the quantity of enzyme necessary to hydrolyze 1 nanomol of substrate per minute.

Table I gives the beta-lactamase activity values measured for the various cultures.

TABLE I

| | BETA-LACTAMASE ACTIVITY (U/ml) | | | | | |
|---|---|---|---|---|---|---|
| | E. Coli HB 101 | | | B. subtilis SMS118 | | |
| Plasmids | O.D. | Viable cells | U/ml | O.D. | Viable cells | U/ml |
| pSM143 | 2.48 | $1 \times 10^9$ | 0.3 | 3.17 | $9.5 \times 10^8$ | 0.37 |
| pSM162 | 2.44 | $9.5 \times 10^8$ | 0.25 | 3.17 | $9.5 \times 10^8$ | 0.41 |
| pSM164 | 2.44 | $9.5 \times 10^8$ | 1.4 | 2.70 | $8 \times 10^8$ | 1.7 |

I claim:

1. A nucleotide sequence capable of inducing high levels of translation of the coding gene for beta-lactamase in B. subtilis and E. coli comprising

```
5' CTTAATTCT 3'
3' CAATTAAGA 5'
``` said sequence being inserted in the hybrid plasmid pSM 164 between the ribosomal recognition site and the starting triplet, ATG, of the coding gene for beta-lactamose.

2. A method of producing beta-lactamase comprising: culturing a strain of B. subtilis or E. coli transformed by said hybrid plasmid pSM 164 according to claim 1 under conditions sufficient to produce beta-lactamase and thereafter recovering beta-lactamase.

3. The method according to claim 2 wherein the strain of B. subtilis is B. subtilis SMS 118 (pSM 164), ATCC 67098.

4. The strain B. subtilis SMS 118 (pSM 164) ATCC 67098.

* * * * *